United States Patent [19]
Kohayakawa

[11] Patent Number: 5,781,275
[45] Date of Patent: Jul. 14, 1998

[54] EYE REFRACTOMETER AND EYE REFRACTIVE POWER MEASURING APPARATUS FOR ELECTRO-OPTICALLY MEASURING THE REFRACTIVE POWER OF THE EYE

[75] Inventor: Yoshimi Kohayakawa, Yokohama, Japan

[73] Assignee: Canon Kabushiki Kaisha, Tokyo, Japan

[21] Appl. No.: 619,333

[22] Filed: Mar. 21, 1996

[30] Foreign Application Priority Data

Mar. 24, 1995 [JP] Japan .................................. 7-091376

[51] Int. Cl.$^6$ ...................................... A61B 3/10
[52] U.S. Cl. ................................ 351/211; 351/205
[58] Field of Search ............................ 351/211, 212, 351/246, 247, 208, 206, 205

[56] References Cited

U.S. PATENT DOCUMENTS

| | | |
|---|---|---|
| 4,609,287 | 9/1986 | Kohayakawa . |
| 4,697,895 | 10/1987 | Sekiguchi et al. . |
| 4,704,012 | 11/1987 | Kohayakawa et al. . |
| 5,144,346 | 9/1992 | Nakamura et al. . |
| 5,231,430 | 7/1993 | Kohayakawa . |
| 5,237,351 | 8/1993 | Kohayakawa et al. . |
| 5,249,003 | 9/1993 | Kohayakawa . |
| 5,280,313 | 1/1994 | Kohayakawa . |
| 5,420,650 | 5/1995 | Kohayakawa . |
| 5,483,305 | 1/1996 | Kohayakawa . |
| 5,506,632 | 4/1996 | Kohayakawa . |

FOREIGN PATENT DOCUMENTS

| | | |
|---|---|---|
| 3-15433 | 1/1991 | Japan . |
| 4-288120 | 10/1992 | Japan . |

*Primary Examiner*—Hung X. Dang
*Attorney, Agent, or Firm*—Fitzpatrick, Cella, Harper & Scinto

[57] ABSTRACT

An eye refractometer includes a beam splitter arranged in front of an eye to be examined for splitting an optical path from the eye to be examined into an optical path for eye observing and an optical path for eye refracting, an eye observing optical system for observing the eye to be examined from a direction oblique to the viewing direction of the eye to be examined with a magnifying optical system by way of the beam splitter, and an eye refracting system for electro-optically measuring the refractive power of the eye to be examined by projecting and receiving a light beam by way of the beam splitter.

11 Claims, 3 Drawing Sheets

EYE REFRACTOMETER AND EYE REFRACTIVE POWER MEASURING APPARATUS FOR ELECTRO-OPTICALLY MEASURING THE REFRACTIVE POWER OF THE EYE

BACKGROUND OF THE INVENTION

1. Field of the Invention

This invention relates to an eye refractometer for use in an eye examination in an ophthalmologic hospital or an optician's store.

2. Related Background Art (1) Heretofore, in an eye refractometer, as disclosed in Japanese Laid-Open Patent Application No. 4-288120, an examiner performs alignment while observing an eye to be examined by means of a magnifying lens, thereby effecting measurement of the eye refractive power.

(2) Also, in an apparatus disclosed in Japanese Laid-Open Patent Application No. 3-15433, a visual target for determining the direction of the patient's visual axis has been projected onto an external object and the external object has been shown to an eye to be examined through a dichroic mirror for directing infrared light from a light source for the measurement of the eye refractive power, to thereby effect measurement of the eye refractive power.

(a) In the above-described example (1) of the prior art, however, the examiner performs alignment while looking into a magnifying lens disposed ahead of the eye to be examined, and this leads to the problem that the examiner's face prevents the examiner from far-viewing the external object.

(b) Also, in the above-described example (2) of the prior art, the visual target is projected onto an external object and presented to the eye to be examined, and this leads to the problem that projection becomes difficult when the object is far.

SUMMARY OF THE INVENTION

It is a first object of the present invention to solve the above-noted problem (a) and to provide an eye refractometer in which an eye to be examined can easily view far outside and an examiner can perform accurate alignment while viewing the eye to be examined.

It is a second object of the present invention to solve the above-noted problem (b) and to provide an eye refractometer which accurately effects measurement of the eye refractive power in the direction of the visual axis without the involvement of accommodation.

DESCRIPTION OF THE PREFERRED EMBODIMENTS

Figure 1:
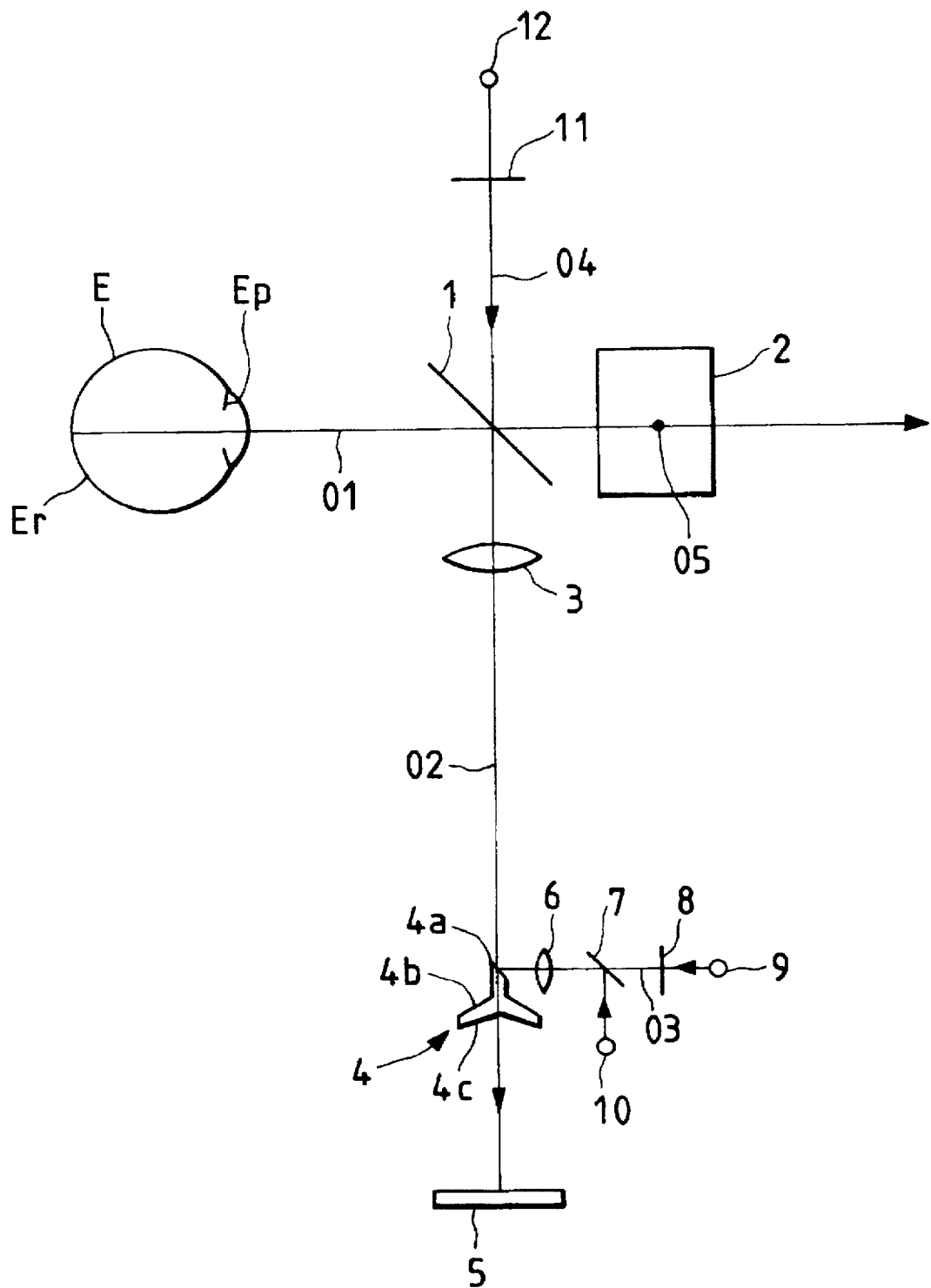
FIG. 1 is a side view of a first embodiment of the present invention.

The present invention will hereinafter be described with respect to some embodiments thereof shown in the drawings.

Referring to FIG. 1, which is a side view of a first embodiment of the present invention, a dichroic mirror 1 reflecting infrared light and partially reflecting visible light and a half mirror 2 are arranged on an optical axis 01 ahead of an eye E to be examined. A light splitting member 4 conjugate with the front eye part of the eye E to be examined, and a two-dimensional array sensor 5, which is a CCD, are arranged in succession on the optical axis 02 of the dichroic mirror 1 in the direction of the reflection thereof. The light splitting member 4 comprises a mirror surface 4a conjugate with the vicinity of a pupil Ep, a lens surface 4b having the lens function and making the fundus Er of an emmetropia conjugate with the two-dimensional array sensor 5, and six inclined surfaces 4c each forming a transmitting area.

On the optical axis 03 of the mirror surface 4a of the light splitting member 4 in the direction of reflection thereof, there are arranged in succession a dichroic mirror 7 for separating near infrared light and visible light from each other, a central small opening stop 8 conjugate with the mirror surface 4a of the light splitting member 4, and a light source 9 for the measurement of refractive power, such as a near infrared LED, and in the direction of incidence of the dichroic mirror 7, there is disposed a point-like light source 10 functioning as the visual target, such as an LED emitting visible light. Also, on the optical axis 04 of the dichroic mirror 1 in the direction of incidence thereof, which is coaxial with the optical axis 02, there are arranged a ring mask 11 having a rink-like opening of the same size as the diameter of a measuring beam of light and conjugate with the pupil Ep with respect to the dichroic mirror 1, and a visible light source 12 being an LED emitting two color lights.

Figure 2:
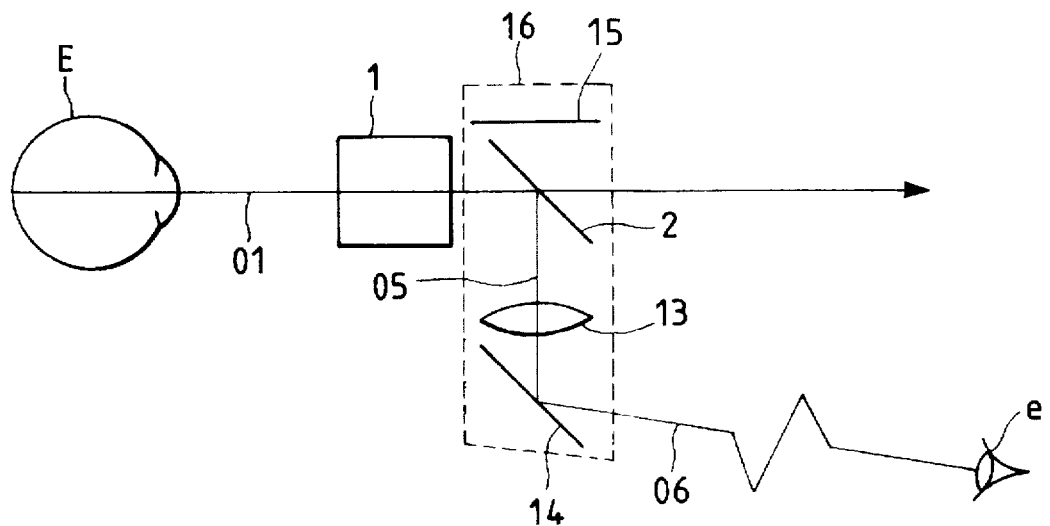
FIG. 2 is a plane view of an observation optical system.

Referring now to FIG. 2, which is a plane view of an observation optical system, a magnifying lens 13 and a mirror 14 are arranged on the optical axis 05 of the half mirror in the direction of reflection thereof, and a non-reflecting black light-intercepting member 15 is provided behind the half mirror 2 in a direction opposite to the optical axis 05. The half mirror 2 and the mirror 14 are not parallel to each other, and the optical axis 06 of the mirror 14 in the direction of reflection thereof is inclined by about 20° with respect to the optical axis 01, which is the visual axis so as to lead to an examiner's eye e. The half mirror 2, the magnifying lens 13, the mirror 14 and the light-intercepting member 15 together form a unit 16, which is rotatable by 180° about the optical axis 01 for the sake of the easy operation by the examiner.

Figure 3:
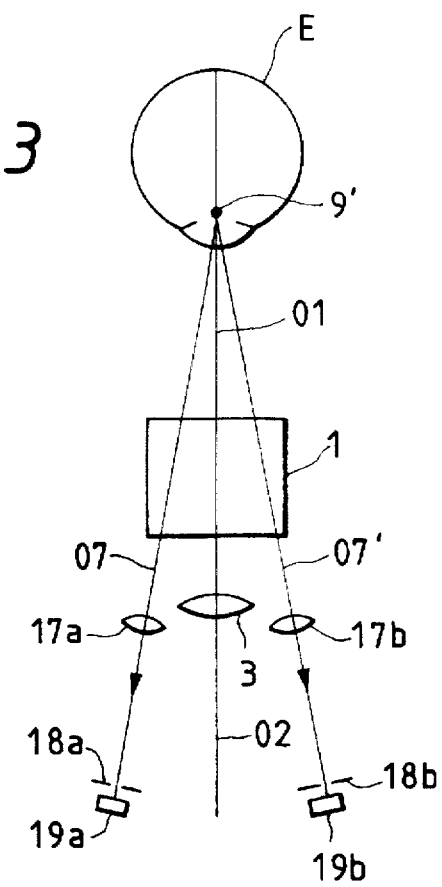
FIG. 3 is a plane view of a position detecting optical system.

Referring to FIG. 3, which is a plane view of a position detecting optical system, the optical axis 01 and the optical axis 02 are extended and depicted on one and the same plane for convenience of explanation. Two optical axes 07 and 07' on the same plane as the optical axes 01 and 02 extend obliquely from the cornea reflected image 9' of the eye E to be examined, and on these optical axes 07 and 07', there are arranged in succession lenses 17a, 17b, stops 18a, 18b and photodetectors 19a, 19b respectively.

A beam of light from the visible light source 12 passes through the ring mask 11, the dichroic mirror 1, the half mirror 2, the magnifying lens 13 and the mirror 14 to the examiner's eye e. The examiner performs alignment via the mirror 14 at a distance of 30–40 cm obliquely ahead of the eye by adjusting the pupil Ep and the ring mask 11 magnified by the magnifying lens 13 concentric with each other. In this case, the light from the direction of transmission of the half mirror 2 is intercepted by the light-intercepting member 15 provided on the extension of the optical axis 05 of the half mirror 2 in the direction of transmission thereof and therefore, the examiner's eye e can see only the direction of reflection of the half mirror 2.

A beam of light from the point-like light source 10, which provides a central fixation visual target on the same axis, as the measuring optical axis passes by way of the dichroic mirror 7, the lens 6, the mirror surface 4a of the light splitting member 4, the lens 3 and the dichroic mirror 1 to the eye E to be examined. The examinee views this visual target and at the same time, views or gauges far outside the apparatus through the dichroic mirror 1 and the half mirror 2. In this case, the optical axis 06 is inclined by about 20° with respect to the optical axis 01 of the visual axis and therefore, the eye E to be examined can view ahead a far distance without being intercepted by the examiner's face.

The light beam of the visual target 10 is projected as a thin beam by way of the mirror portion 4a of a small area conjugate with the vicinity of the pupil Ep and therefore is not so blurred irrespective of the refractive power of the eye E to be examined, and the direction of the visual axis can be determined accurately. Thus, when the measurement of the refractive power is done in a state in which the examinee is viewing this beam of light, the measurement is performed in the direction of the visual axis and therefore, an accurate eye refraction value can be obtained.

Figure 4:
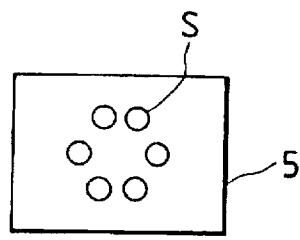
FIG. 4 is a front view of a two-dimensional array sensor.

A beam of light from the light source 9 for the measurement of the refractive power passes through the central small opening stop 8 and the dichroic mirror 7 and is once imaged at the center of the mirror portion 4a of the light splitting member 4. Accordingly, it does not happen that the beam of light impinges on the edge of the mirror portion 4a and becomes harmful light. The beam of light reflected by the mirror portion 4a is projected as a spotlight onto the center of the fundus Er of the eye from the center of the pupil Ep of the eye E to be examined through the lens 3 and the dichroic mirror 1. The reflected light from the fundus Er of the eye returns along the same optical path and passes through the six transmitting areas around the optical axis 02 of the light splitting member 4, and six spot beams of light S as shown in FIG. 4 are imaged on the two-dimensional array sensor 5. The output signal of this two-dimensional array sensor 5 is introduced into a computer in the apparatus, and the position of each spot beam of light S is calculated to thereby obtain a refractive value including astigmatism.

During alignment as well, the light source 9 for the measurement of the refractive power is continuously turned on, and as shown in FIG. 3, the cornea reflected image 9' thereof is detected by the photodetectors 19a, 19b from two directions through the lenses 17a, 17b and the stops 18a, 18b. When the eye E to be examined has come to a predetermined position, the cornea reflected image 9' is imaged on the stops 18a, 18b by the lenses 17a, 17b, and the signals of the photodetectors 19a, 19b at this time become maximum. When the signals of the both photodetectors 19a, 19b become equal to or greater than a predetermined value and the difference between those signals becomes equal to or less than a predetermined value, the computer determines that the position is correct, and automatically starts the measurement of the refractive power.

The visible light source 12 is changed from red light to green light when the computer determines that the position is correct to a certain degree. Also, if the stops 18a, 18b are not used and a photoelectric sensor comprising square shaped four divided elements is used instead of the detectors 19a, 19b, positional information in the direction of the optical axis 01 and in a direction perpendicular thereto will be obtained from the relation among the signals of those elements and therefore, the visible light source 12 may be designed to emit red light and green light alternately only when the direction of the optical axis 01 has become right, and to emit green light when both directions have become right. If the device is designed to separately indicate the alignment information of the direction of the optical axis 01 and the eccentricity perpendicular thereto, the alignment will become easier.

In addition to the automatic measurement start by the signal of such a detecting optical system in FIG. 3, the device is designed to effect measurement when the examiner depresses a switch. In most cases, when the examinee is viewing ahead, the cornea image 9' of the light source present in that direction comes to the center of the pupil Ep and therefore, the alignment by the detecting optical system and the alignment by the observation optical system coincide with each other. In the case of a squinting eye, a corneal reflection does not come out to the center of the pupil Ep and therefore, measurement is effected by intercepting the optical path of the other eye not being measured.

As another system of alignment, the device is designed to automatically start measurement if only the optical axis 01 is within a predetermined range, and further, there can be provided such a sequence that if the uniformity of the quantity of light of the spot beams of light S on the two-dimensional array sensor 5 is good, it is judged that the alignment in the direction of the optical axis 01 is also right, the measurement of eye refractive power is effected, and an eye refractive value is displayed on a display, not shown. For the detection of the direction of the optical axis 01 at this time, one-dimensional optical position sensors can be disposed at the positions at which the cornea reflected image 9' is formed by the lenses 17a, 17b shown in FIG. 3, so that the direction of the optical axis 01 may be found from the relation between the image positions on both sides. The device may also be designed to indicate by sound or the like that measurement has been effected properly.

In the above-described embodiment, the light source 9 for the measurement of refractive power is used also for alignment, but alternatively, a discrete light source may be provided for the detection of cornea-reflected light therefrom, and the two-dimensional array sensor 5 may also be used for the alignment as well. Also, when the eye E to be examined is not viewing the direction of the measuring optical axis, corneal reflection does not take place at the center of the pupil and thereof ore, if the above-described alignment system is adopted, accurate measurement of the eye refractive e power c an be effected even for an examinee like an infant whose visual axis is not stable.

Figure 5:
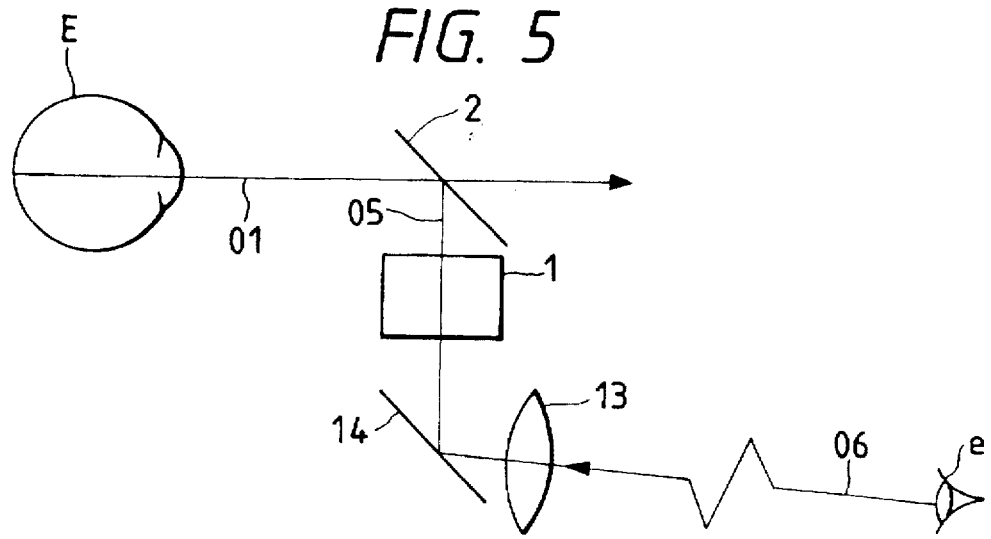
FIG. 5 is a side view of an observation optical system in a second embodiment of the present invention.

FIG. 5 is a plane view of an observation optical system in a second embodiment of the present invention. In FIG. 5, the same reference numerals as those in FIG. 2 designate the same members. The dichroic mirror 1 reflecting the refractive power measuring beam of light is disposed between the half mirror 2 and the mirror 14, and in the other points, this embodiment is similar to the first embodiment, and a similar operational effect is obtained.

Figure 6:
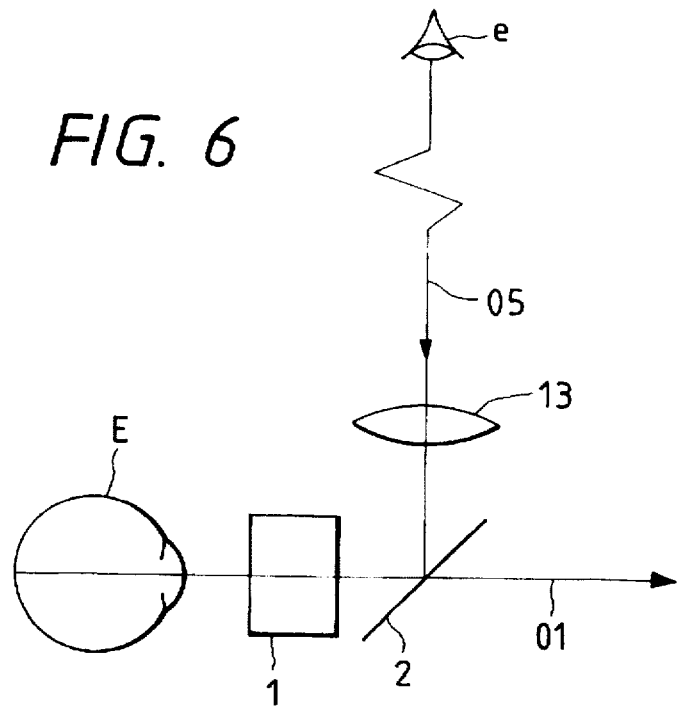
FIG. 6 is a side view of an observation optical system in a third embodiment of the present invention.

FIG. 6 is a plan view of an observation optical system in a third embodiment of the present invention. In this third embodiment, the mirror 14 is not used, but reflected light directly passes from the lens 13 to the examiner's eye e, and on the other points, this embodiment is similar to the first embodiment. The examiner may adjust a ring image reflected from a side of the examinee to the half mirror 2 to the pupil Ep. In this case, movement right and left becomes opposite, but this will pose no problem if the examiner becomes accustomed thereto.

As described above, the observation optical path is caused to branch off by a light branching-off member and a magnifying lens is provided in the observation optical path, whereby the examinee can easily view a far external object without his view being intercepted by the examiner's face, and the examiner can view the magnified eye to be examined and effect accurate alignment.

Also, by the use of the central fixation visual target provided in the direction of the optical axis of the measuring optical system, the measurement of the eye refractive power can be effected through the light splitting member partially reflecting and transmitting visible light therethrough, thereby objectively measuring the refractive power in the direction of the visual axis in a state in which the eye to be examined is free from accommodation due to far external viewing.

What is claimed is:

1. An eye refractometer, comprising:
    a beam splitter arranged in front of an eye to be examined for splitting an optical path from the eye to be examined into an optical path for eye observing and an optical path for eye refracting;
    an eye observing optical system for observing the eye to be examined from a direction oblique to the viewing direction of the eye to be examined with a magnifying optical system by way of said beam splitter; and
    an eye refracting system for electro-optically measuring the refractive power of the eye to be examined by projecting a light beam to the eye receiving a light beam from the eve by way of said beam splitter.

2. An eye refractometer according to claim 1, wherein said eye observing optical system is rotatable around the viewing axis of the eye to be examined.

3. An eye refractometer according to claim 1, wherein said eye observing optical system includes a partially reflecting mirror arranged on the viewing direction of the eye, a mirror, and magnifying optics arranged in the same plane.

4. An eye refractometer according to claim 1, wherein an alignment mark is projected by way of said beam splitter.

5. An eye refractometer, comprising:
    a beam splitter arranged in front of an eye of an examinee for splitting an optical path from the eye of the examinee into an optical path for viewing of the examinee and an optical path for eye refracting;
    an eye refracting system for electro-optically measuring the refractive power of the eye of the examinee by projecting a light beam to the eye and receiving a light beam from the eye by way of said beam splitter; and
    a fixation target projecting system for projecting a fixation target to the eye of the examinee along the optical path of said eye refracting system by way of said beam splitter.

6. An eye refractometer according to claim 5, further comprising a beam splitter arranged in an optical system of said eye refracting system through which said fixation target is projected.

7. An eye refractometer according to claim 6, wherein said fixation target is a spot on the optical axis of said eye refracting system.

8. An eye refractometer, comprising:
    an eye observing optical system including a beam splitter arranged in an optical path for viewing of an examinee, a reflection member, and a magnifying optical member arranged in the same plane; and
    an eye refracting system for electro-optically measuring the refractive power of the eye of the examinee by projecting a light beam to the eve and receiving a light beam from the eve by way of another beam splitter arranged in the vicinity of said beam splitter;
    wherein the eye of the examinee is observable from a direction oblique to the viewing direction of the eye through said reflection member.

9. An eye refractometer according claim 8, wherein the observing direction of said eye observing optical system forms an angle from the optical path for viewing of the examinee.

10. An eye refractometer comprising:
    a beam splitter arranged in front of an eye to be examined;
    an eye refracting system for electro-optically measuring the refractive power of the eye gazing outside the apparatus through said beam splitter by projecting a light beam to the eye and receiving a light beam from the eye by way of said beam splitter; and
    an alignment detecting system detecting the cornea reflection of a light source and effecting initiation of automatic measurement of said eye refracting system on the basis of said detecting.

11. An eye refractor power measuring apparatus comprising:
    an observing optical system for optically observing the eye to be examined;
    an eye refractive power measuring system for electro-optically measuring the refractive power of the eye to be examined by projecting a light beam to the eye and receiving a light beam from the eye;
    an alignment detecting system detecting the position of the eye in the direction of the optical axis of said eye refractive power measuring system and in a direction perpendicular to the optical axis; and
    an alignment indication means for indicating the position of the eye according to the detection of said alignment detecting system.

* * * * *

UNITED STATES PATENT AND TRADEMARK OFFICE
CERTIFICATE OF CORRECTION

PATENT NO. : 5,781,275

DATED : July 14, 1998

INVENTOR : YOSHIMI KOHAYAKAWA

It is certified that error appears in the above-identified patent and that said Letters Patent is hereby corrected as shown below:

COLUMN 1,
Line 53, "plane" should read --plan--.
Line 54, "plane" should read --plan--.

COLUMN 2,
Line 28, "rink-like" should read --ring-like--.

COLUMN 3,
Line 5, "axis," should read --axis--.
Line 6, "axis" should read --axis,--.
Line 10, "gauges" should read --gazes-.
Line 54 "become" should read --become a--.

COLUMN 4,
Line 47, "theref ore" should read --therefore--.
Line 49, "e power" should read --power--, and "c an" should read --can--.

COLUMN 5,
Line 31, "projecting a light beam to the eye receiving a light" should read --projecting a light beam to the eye and receiving a light--.

UNITED STATES PATENT AND TRADEMARK OFFICE
CERTIFICATE OF CORRECTION

PATENT NO. : 5,781,275

DATED : July 14, 1998

INVENTOR : YOSHIMI KOHAYAKAWA

It is certified that error appears in the above-identified patent and that said Letters Patent is hereby corrected as shown below:

<u>COLUMN 6</u>,
Line 16, "eve" should read --eye--.
Line 22, "according" should read --according to--.
Line 37, "refractor" should read --refractive--.

Signed and Sealed this

Fifteenth Day of June, 1999

Attest:

Q. TODD DICKINSON

Attesting Officer     Acting Commissioner of Patents and Trademarks